L. T. J. LUBIN.

HERNIA TRUSSES.

No. 7,896. Reissued Sept. 25, 1877.

WITNESSES

J. D. Gould.

Geo. H. Earl.

INVENTOR

Leon T. J. Lubin

Per Brown Bros.

Attorneys.

N. PETERS, PHOTO-LITHOGRAPHER, WASHINGTON, D. C.

UNITED STATES PATENT OFFICE.

LEON T. J. LUBIN, OF BOSTON, MASSACHUSETTS.

IMPROVEMENT IN HERNIA-TRUSSES.

Specification forming part of Letters Patent No. 168,264, dated September 28, 1875; Reissue No. 7,896, dated September 25, 1877; application filed July 19, 1877.

*To all whom it may concern:*

Be it known that I, LEON T. J. LUBIN, of Boston, in the county of Suffolk and State of Massachusetts, have invented Improvements in Hernia-Trusses, of which the following is a specification:

This invention relates to hernia-trusses, more particularly designed for umbilical hernia, but applicable to other hernia-trusses.

The improvements are fully hereinafter described, and pointed out in the claims, and a preliminary description is therefore not deemed essential.

Figure 1:
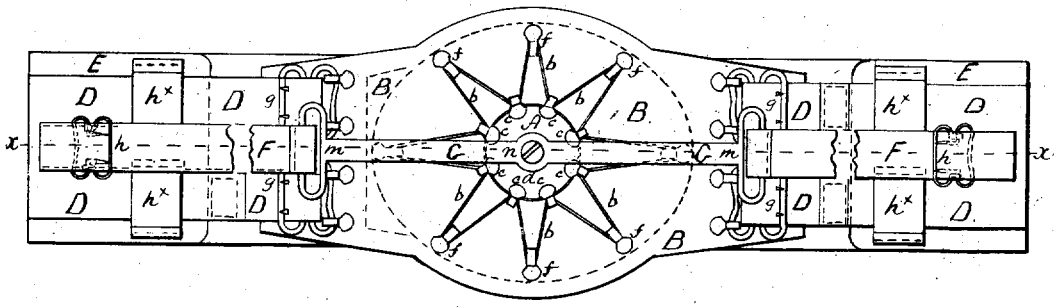
Figure 2:
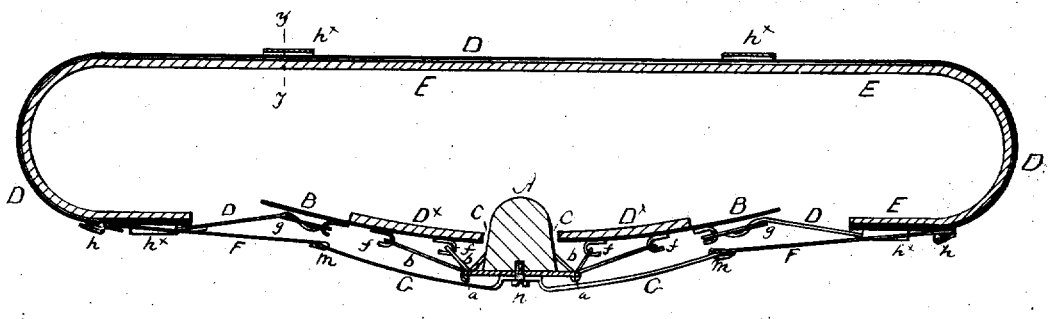
Figure 3:
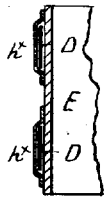

In the accompanying plate of drawings, Figure 1 is a face view of a hernia-pad embracing the several features of the present improvements; Fig. 2, a sectional view, substantially on line *x x*, Fig. 1; Fig. 3, a cross section on line *y y*, Fig. 2; and Fig. 4, a face view, showing a modification to be hereinafter particularly referred to.

In the drawings, A represents the hernia-pad. This pad A is to be made of any suitable form and of any suitable material or materials, and the form shown is particularly applicable for umbilical hernia. B, a padded plate open at the center C. The pad A is loose in the opening C of pad, and projects at its padded side D×. *a*, a lip surrounding pad A. This lip *a* of pad A bears against the outside face of pad B, and limits the projection of the pad A through the central opening C of pad B. *b*, an endless elastic cord or string. This endless cord *b* passes continuously about a series of hooks, C C, at the outer end of the hernia-pad A, and a series of hooks, *f*, on the outer face *g* of the padded plate B, and thus the hernia-pad A is connected to the padded plate B, and hung and suspended in its central opening C. D D, two elastic webbings or straps. These elastic straps D are buckled at each end, as at *g g*, to the outside of the padded plate B, and between their two ends they encircle or pass about the outside of a single non-elastic band, E, and to this band they are confined by stationary loops *h*×, through which they are free to play. F, non-elastic straps, buckled at *h*, one to each end of the non-elastic band E, and both hung to the loops *m* of the bent spring-band G fastened, by a set-screw, *n*, to the center of the hernia-pad A.

The hernia-pad A and all its attachments herein described are particularly applicable to umbilical hernia; and to use it for this purpose, first place the band E about the body, with hernia-pad A in the umbilicus, and then properly buckle the elastic straps D of the band E and the non-elastic straps F of the hernia-pad A, which secures the truss in position.

The herein-described connection of the hernia-pad with its holder allows the pad to roll and tip, and thus to adjust itself as may be necessary; and, as such connection is made through the medium of an elastic cord, *b*, elasticity is given to such rolling movement of the pad, and the pad, under the tension of the cord *b*, is made to follow and keep its bearing in the umbilicus in all directions.

The spring-band G holds the hernia-pad to its position in the umbilicus, and, applied as herein described, it offers no practical obstruction to the described roll of the hernia-pad.

The elastic straps D encircling the band E, as herein described, allow the padded plate B, which carries the hernia-pad, to yield to the outward movements of the body from the breathing or coughing, &c., of the wearer; and by the non-elastic connection herein described of the band E with the pressure-spring G of the hernia-pad, the hernia-pad, in these outward movements of the body, is not only held to its position in the umbilicus, but its pressure therein through its spring G is proportionately increased, thus entirely overcoming and counterbalancing the outward thrust of the hernia from such causes, which, obviously, prevents any disturbance in the hold of the hernia by the hernia-pad of the truss.

Figure 4:
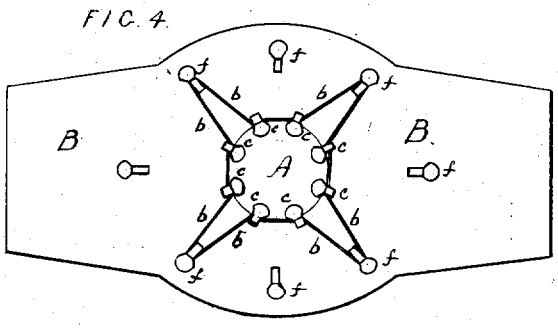

The arrangement herein described of the elastic cord *b* to give elasticity to the rolling movement of the hernia-pad is a most convenient one for changing the degree or extent of its elastic action on the hernia-pad, as it is only necessary for such adjustment of its elastic action on the hernia-pad to hook it upon more or less of the two series of hooks *c c* and *f f*, one change being shown by Fig. 4; and, furthermore, the cord *b* can be readily removed and another one substituted for it.

For securing elasticity to the roll of the hernia-pad, other forms of springs than that herein particularly described may be used— as, for instance, spiral springs or bent springs, connected to and stretched from the hernia-pad to its holder, substantially like the endless cord; but the arrangement of the elastic cord herein described is preferable, as it is most efficient, and, besides, it is cheap and easy of application and adjustment.

The non-elastic band E, encircled by the elastic straps D, shields the elastic straps from direct contact with the body of the wearer, and thus protects them against injury from the perspiration of the body.

Between the ends of the bands E and the hernia-pad plate B the elastic straps are continued by non-elastic webbing, as at L, to protect the elastic band against the perspiration of the body not covered by the hernia-pad plate B and the band E.

Having now described my invention, what I claim, and desire to secure by Letters Patent, is—

1. The hernia-pad A and holder pad or plate B, the two applied and connected together by an elastic cord, *b*, substantially as described, for the purpose specified.

2. The hernia-pad A, arranged to move in and out of its holder pad or plate B, the spring-band G, and the elastic straps D D, and a non-elastic band, E, all connected together and arranged substantially as herein described, and for the inward movement or pressure of the hernia-pad A in the outward movement of the holder-pad B, substantially as specified.

3. The non-elastic band E, with its loops $h^{\times}$, in combination with the elastic strap or straps D, substantially as and for the purpose described.

LEON T. J. LUBIN.

Witnesses:
S. M. VAN ALSTINE,
EDWIN W. BROWN.